US012576259B2

(12) United States Patent
Janzen et al.

(10) Patent No.: US 12,576,259 B2
(45) Date of Patent: Mar. 17, 2026

(54) AUTOMATIC POWER ADJUSTMENTS BASED ON TUBING STATE DETECTION FOR TUBE WELDING DEVICES

(71) Applicant: Terumo BCT, Inc., Lakewood, CO (US)

(72) Inventors: Jesse Janzen, Golden, CO (US); Jeremy Kolenbrander, Brighton, CO (US); James Ladtkow, Broomfield, CO (US)

(73) Assignee: Terumo BCT, Inc., Lakewood, CO (US)

( * ) Notice: Subject to any disclaimer, the term of this patent is extended or adjusted under 35 U.S.C. 154(b) by 125 days.

(21) Appl. No.: 18/444,252

(22) Filed: Feb. 16, 2024

(65) Prior Publication Data

US 2024/0325716 A1     Oct. 3, 2024

Related U.S. Application Data

(60) Provisional application No. 63/455,817, filed on Mar. 30, 2023.

(51) Int. Cl.
A61M 39/14          (2006.01)

(52) U.S. Cl.
CPC ......... A61M 39/14 (2013.01); A61M 2207/10 (2013.01)

(58) Field of Classification Search
CPC .......................... A61M 39/14; A61M 2207/10
See application file for complete search history.

(56) References Cited

U.S. PATENT DOCUMENTS 5,507,178 A     4/1996   Dam
5,785,692 A  *  7/1998   Attermeier .............. A61M 5/24
                                                          604/905

(Continued)

FOREIGN PATENT DOCUMENTS

EP        0649727 B1     5/2002
EP        1438981 B1     2/2009

(Continued)

OTHER PUBLICATIONS

Machine translation JPH11178891A (Year: 1999).*

(Continued)

*Primary Examiner* — Abbas Rashid
*Assistant Examiner* — Wayne K. Swier
(74) *Attorney, Agent, or Firm* — Harness, Dickey & Pierce, P.L.C.

(57)          ABSTRACT
A tube welding device for joining tubes includes a first tube-holding assembly configured to receive a first portion of a first tube and a first portion of a second tube, and a second tube-holding assembly configured to receive a second portion of the first tube and a second portion of the second tube. The first tube-holding assembly includes a first detector, and the second tube-holding assembly includes a second detector. The first and second detectors are configured to detect the presence or absence of fluid in the respective tubes and to generate signals indicative of the same. The tube welding device includes a controller configured to receive the signals, to select an appropriate tube-joining temperature in response to the presence or absence of fluid in the first and second tubes, and to cause an appropriate power level to be sent to a wafer to generate the tube-joining temperature.

18 Claims, 4 Drawing Sheets

(56) References Cited

U.S. PATENT DOCUMENTS

| | | | |
|---|---|---|---|
| 7,657,996 B2 | 2/2010 | Sano et al. | |
| 11,312,087 B2 | 4/2022 | Kanemaru | |
| 2007/0142960 A1 | 6/2007 | Bollinger et al. | |
| 2022/0234303 A1 | 7/2022 | Madsen et al. | |

FOREIGN PATENT DOCUMENTS

| | | | | | |
|---|---|---|---|---|---|
| GB | 2275340 A | * | 8/1994 | ............ | G01M 3/184 |
| JP | H11178891 A | * | 7/1999 | ....... | B29C 66/73921 |
| WO | WO-2004020179 A1 | * | 3/2004 | ......... | B29C 66/0018 |
| WO | WO-2005002832 A1 | * | 1/2005 | ......... | B29C 66/0018 |
| WO | WO-2020262194 A1 | * | 12/2020 | ......... | B29C 65/2046 |

OTHER PUBLICATIONS

Machine translation WO2004020179A1 (Year: 2004).*
Machine translation WO2005002832A1 (Year: 2005).*
Machine translation WO2020262194A1 (Year: 2020).*
International Search Report for corresponding International Patent Application No. PCT/2024/016395 dated Jun. 18, 2024 (3 pages).
Written Opinion for corresponding International Patent Application No. PCT/2024/016395 dated Jun. 18, 2024 (7 pages).

* cited by examiner

AUTOMATIC POWER ADJUSTMENTS BASED ON TUBING STATE DETECTION FOR TUBE WELDING DEVICES

CROSS-REFERENCE TO RELATED APPLICATIONS

This application claims the benefit of U.S. Provisional Patent Application No. 63/455,817 filed on Mar. 30, 2023. The entire disclosure of the above application is incorporated herein by reference.

FIELD

The present disclosure relates to tube welding devices configured to automatically adjust one or more parameters as applied to a wafer (for example, in response to the presence or absence of a fluid in tubes to be joined) and methods of using the same.

BACKGROUND

This section provides background information related to the present disclosure which is not necessarily prior art.

Tube welding machines (also referred to as tube welding devices) are used for connecting closed end tubes which are often connected to bags or similar containers to carry, for example, blood or blood components. Tube welding devices commonly include first and second tube-holding assemblies (e.g., first and second clamps) configured to receive first and second tubes and a space between the first and second tube-holding assemblies configured to receive a wafer (e.g., heated blade), where the tubing welding device is configured to send energy to the space such that the wafer can be heated to desired temperatures. A process used in conjunction with a tubing welding device may include sending energy to the wafer to heat the wafer to a desired temperature and urging the heated wafer into contact with each tube held by the tube-holding assemblies to temporarily seal together opposing surfaces of the respective tubes and create molten tube ends. At least a portion of one or both of the first and second tube-holding assemblies may then be moved to align and join together the molten tube ends of the first and second tubes. The joint may be cooled and subjected to a stress to open the temporary seals providing fluid communication between the as-joined first and second tubes.

Tubing that includes fluid often requires a higher wafer temperature to produce an adequate weld as compared to tubing where fluid is absent. Common methods for using tubing welding devices often address these differing requirements by selecting a median temperature that is between the higher and lower temperatures. These approaches, however, often result in burning tubing when fluid is absent and week welds when fluid is present. It would be desirable to develop systems, and processes for using the same, that can address these challenges.

SUMMARY

This section provides a general summary of the disclosure and is not a comprehensive disclosure of its full scope or all of its features.

In various aspects, the present disclosure provides a tube welding device for joining two tubes.

In at least one example embodiment, the tube welding device may include a first tube-holding assembly that can be configured to receive a first portion of a first tube and a first portion of a second tube. The first tube-holding assembly may include a first detector, where the first detector may be configured to detect the presence or absence of fluid in the first tube and to generate a first signal indicative of the same. The tube welding device may further include a second tube-holding assembly that can be configured to receive a second portion of the first tube and a second portion of the second tube. The second tube-holding assembly may include a second detector, where the second detector may be configured to detect the presence or absence of fluid in the second tube and to generate a second signal indicative of the same. The tube welding device may also include a wafer disposed between at least a portion of the first tube-holding assembly and at least a portion of the second tube-holding assembly. The tube-welding device may be configured to heat the wafer to a tube-joining temperature and to bring the wafer heated to the tube-joining temperature into contact with the first and second tubes. The tube welding device may also include a controller that is configured, for example, to receive the first and second signals, to select the tube-joining temperature in response to the presence or absence of fluid in the first and second tubes, and to cause an appropriate power level to be sent to the wafer to generate the tube-joining temperature.

In at least one example embodiment, when fluid is absent from the first and second tubes, the controller may be configured to send a first power level to the wafer to generate a first tube-joining temperature.

In at least one example embodiment, when fluid is present in one of the first and second tubes and is absent from the other of the first and second tubes, the controller may be configured to send a second power level to the wafer to generate a second tube-joining temperature that is greater than the first tube-joining temperature.

In at least one example embodiment, when fluid is present in both of the first and second tubes, the controller may be configured to send a third power level to the wafer to generate a third tube-joining temperature that is greater than the second tube-joining temperature.

In at least one example embodiment, the first tube-holding assembly may include a first cavity for receiving the first portion of the first tube and a second cavity for receiving the first portion of the second tube.

In at least one example embodiment, the second tube-holding assembly may include a third cavity for receiving the second portion of the first tube and a fourth cavity for receiving the second portion of the second tube.

In at least one example embodiment, in a first position the first tube-holding assembly may be aligned with the second tube-holding assembly such that the first cavity of the first tube-holding assembly is in line with the third cavity of the second tube-holding assembly and the second cavity of the first tube-holding assembly is in line with the third cavity of the second tube-holding assembly.

In at least one example embodiment, the first detector may be disposed within the first cavity of the first tube-holding assembly, and the second detector may be disposed within the fourth cavity of the second tube-holding assembly.

In at least one example embodiment, the first tube-holding assembly may include a first bottom portion and a first top portion, where the first bottom portion may include a first crevice and a second crevice, the first top portion may include a third crevice and a fourth crevice, the first crevice of the first bottom portion and the third crevice of the first top portion may align to form the first cavity, and the second crevice of the first bottom portion and the fourth crevice of the first top portion may align to form the second cavity. The second tube-holding assembly may include a second bottom portion and a second top portion, the second bottom portion may include a first crevice and a second crevice, the second top portion may include a third crevice and a fourth crevice, the first crevice of the second bottom portion and the third crevice of the second top portion may align to form the third cavity, and the second crevice of the second bottom portion and the fourth crevice of the second top portion may align to form the fourth cavity. The first detector may be disposed within the first crevice of the first bottom portion of the first tube-holding assembly, and the second detector may be disposed within the second crevice of the second bottom portion of the second tube-holding assembly.

In at least one example embodiment, the first tube-holding assembly may include a first bottom portion and a first top portion, where the first bottom portion may include a first crevice and a second crevice, the first top portion may include a third crevice and a fourth crevice, the first crevice of the first bottom portion and the third crevice of the first top portion may align to form the first cavity, and the second crevice of the first bottom portion and the fourth crevice of the first top portion may align to form the second cavity. The second tube-holding assembly may include a second bottom portion and a second top portion, the second bottom portion may include a first crevice and a second crevice, the second top portion may include a third crevice and a fourth crevice, the first crevice of the second bottom portion and the third crevice of the second top portion may align to form the third cavity, and the second crevice of the second bottom portion and the fourth crevice of the second top portion may align to form the fourth cavity. The first detector may be disposed within the third crevice of the first top portion of the first tube-holding assembly, and the second detector may be disposed within the fourth crevice of the second top portion of the second tube-holding assembly.

In at least one example embodiment, the first detector may be disposed within the second cavity of the first tube-holding assembly, and the second detector may be disposed within the third cavity of the second tube-holding assembly.

In at least one example embodiment, the tube welding device may be configured to move the at least a portion of at least one of the first tube-holding assembly and the second tube-holding assembly such that the first tube-holding assembly and the second tube-holding assembly are in a second position where the first cavity of the first tube-holding assembly may be brought in line with the fourth cavity of the second tube-holding assembly.

In at least one example embodiment, the tube welding device may be configured to move the at least a portion of at least one of the first tube-holding assembly and the second tube-holding assembly such that the first tube-holding assembly and the second tube-holding assembly are in a second position where the second cavity of the first tube-holding assembly may be brought in line with the third cavity of the second tube-holding assembly.

In at least one example embodiment, the first and second detectors may each include a push switch, a Hall-effect sensor, an optical switch, a magnetic switch, an inductive sensor, a capacitive sensor, an ultrasonic sensor, or any combination thereof.

In various aspects, the present disclosure provides a method for using a tube welding device.

In at least one example embodiment, the method may include receiving, by a processor, input from a first sensor aligned with a first clamp configured to receive at least a portion of a first tube, the first sensor configured to detect a presence or absence of fluid in the first tube; receiving, by a processor, input from a second sensor aligned with a second clamp configured to receive at least a portion of a second tube, the second sensor configured to detect a presence or absence of fluid in the second tube; and supplying, by a processor, power to a wafer disposed between the first clamp and the second clamp, where an amount of the supplied power may be at a first preselected power level when fluid is absent in both the first tube and the second tube, at a second preselected power level greater than the first power level when fluid is present in one of the first tube and the second tube and absent in the other of the first tube and the second tube, and at a third preselected power level greater than the second power level when fluid is present in both the first tube and the second tube.

In at least one example embodiment, the method may further include moving the wafer, as or after the power is applied the wafer, from a first wafer position to a second wafer position to form a first molten tube end in the first tube and a second molten tube end in the second tube.

In at least one example embodiment, the method may further include moving at least a portion of the first clamp or of the second clamp form a first clamp position to a second clamp position to align and join the first molten tube end and the second molten tube end to form a continuous tube.

In various aspects, the present disclosure provides a method for preparing a continuous tube from a first tube and a second tube.

In at least one example embodiment, the method may include heating a wafer disposed between a first clamp configured to receive a portion of a first tube and including a first sensor and a second clamp configured to receive a portion of a second tube and including a second sensor. The first sensor may be configured to detect a presence or absence of fluid in the first tube. The second sensor may be configured to detect a presence or absence of fluid in the second tube. The wafer may be heated to a first preselected temperature when fluid is absent from both the first tube and the second tube, a second preselected temperature when fluid is present in one of the first tube and the second tube and absent from the other of the first tube and the second tube, and a third preselected temperature when fluid is present in both of the first tube and the second tube. The method may further include, as or after the wafer is heated, moving the wafer from a first wafer position to a second wafer position to form a first molten tube end and a second molten tube end, and/or moving at least a portion of the first clamp position or of the second clamp position from a first clamp position to a second clamp position to align and join the first molten tube end and the second molten tube end to form the continuous tube.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

Figures 1A, 1B:
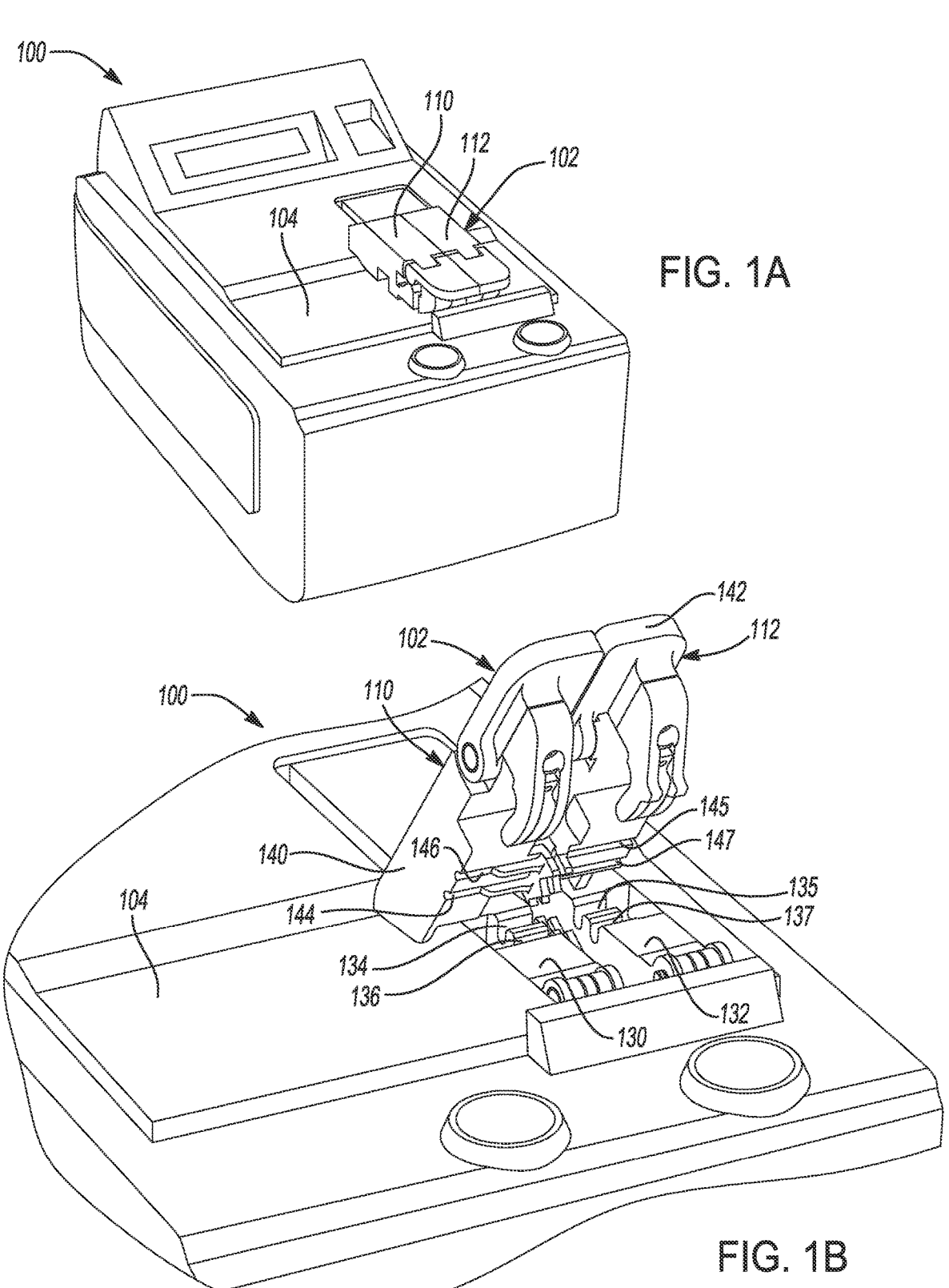
FIG. 1A is a perspective view of an example tube welding device including a first tube-holding assembly and a second tube-holding assembly, where the first and second tube-holding assemblies are in a closed position, in accordance with at least one example embodiment of the present disclosure.
FIG. 1B is a perspective view of the example tube welding device of FIG. 1A where the first and second tube-holding assemblies are in an open position in accordance with at least one example embodiment of the present disclosure.
Figure 1C:
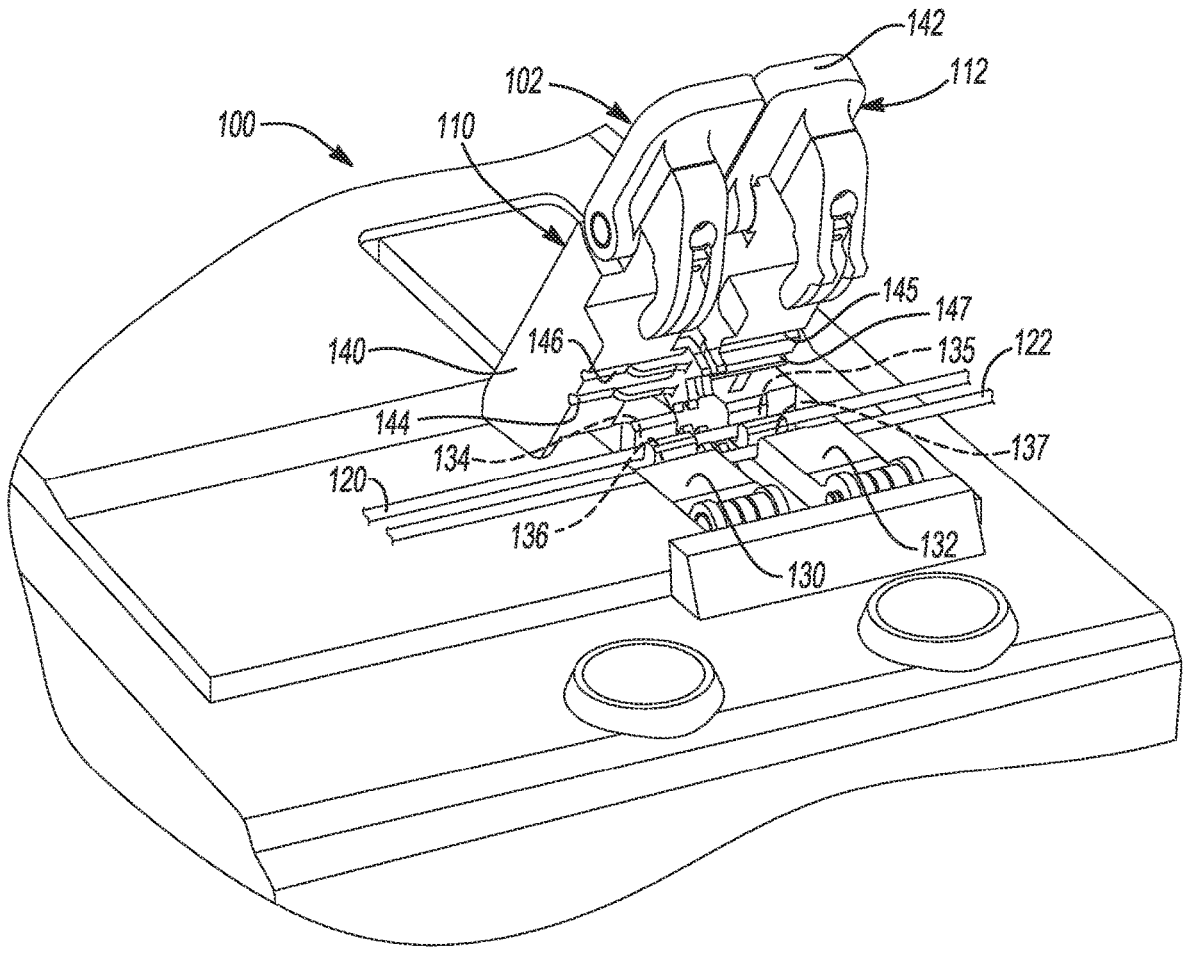
FIG. 1C is a perspective view of the example tube welding device of FIG. 1B where the first and second tube-holding assemblies receive portions of a first tube and a second tube in accordance with at least one example embodiment of the present disclosure.
Figures 1D, 1E, 2:
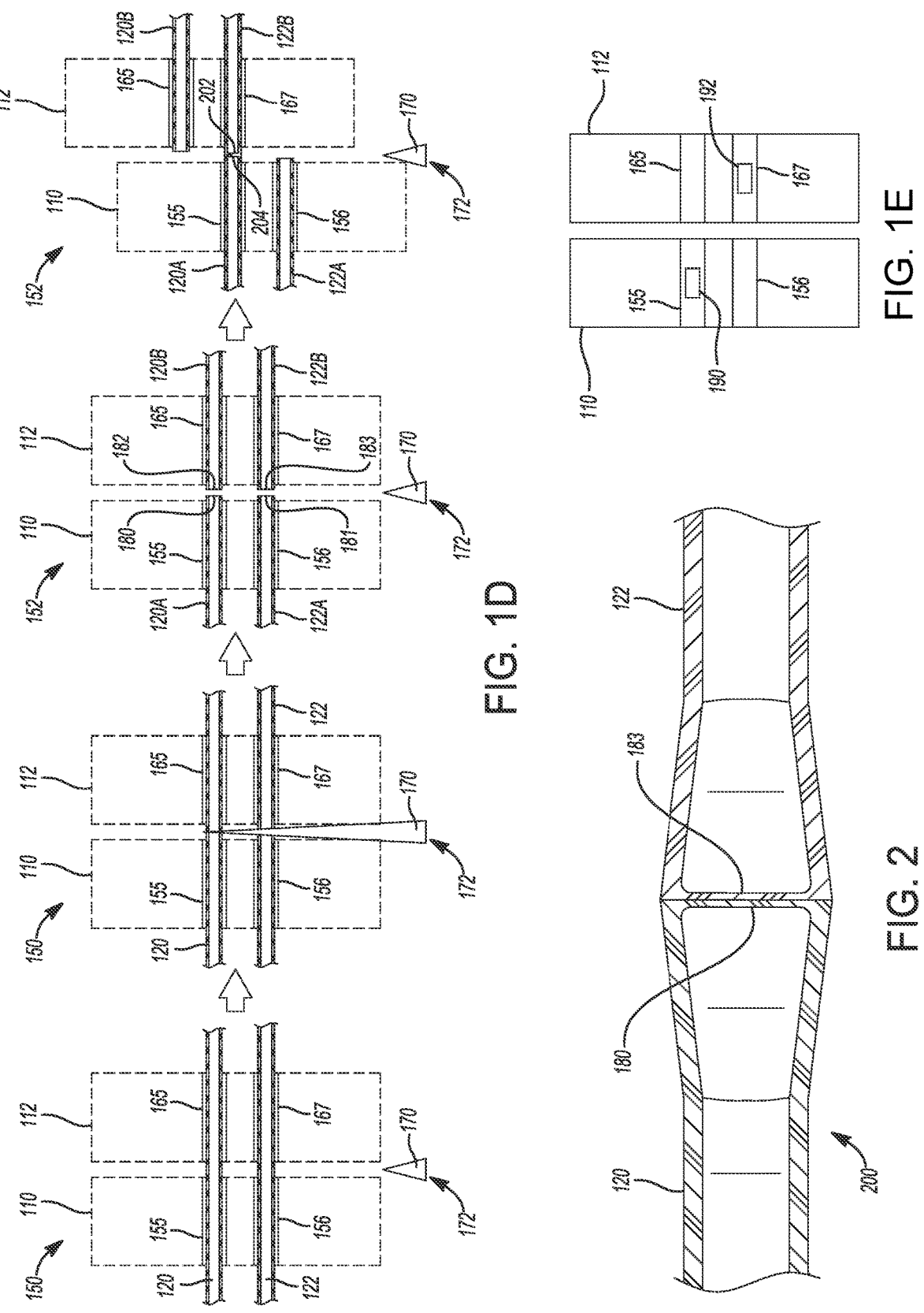
FIG. 1D is a simplified illustration of the movement of the first and second tube-holding assemblies as illustrated in FIGS. 1A-1C in accordance with at least one example embodiment of the present disclosure.
FIG. 1E is a top-down view of the example tube welding device of FIG. 1A where each of the first and second tube-holding assemblies include one or more fluid detectors in accordance with at least one example embodiment of the present disclosure.
Figure 3:
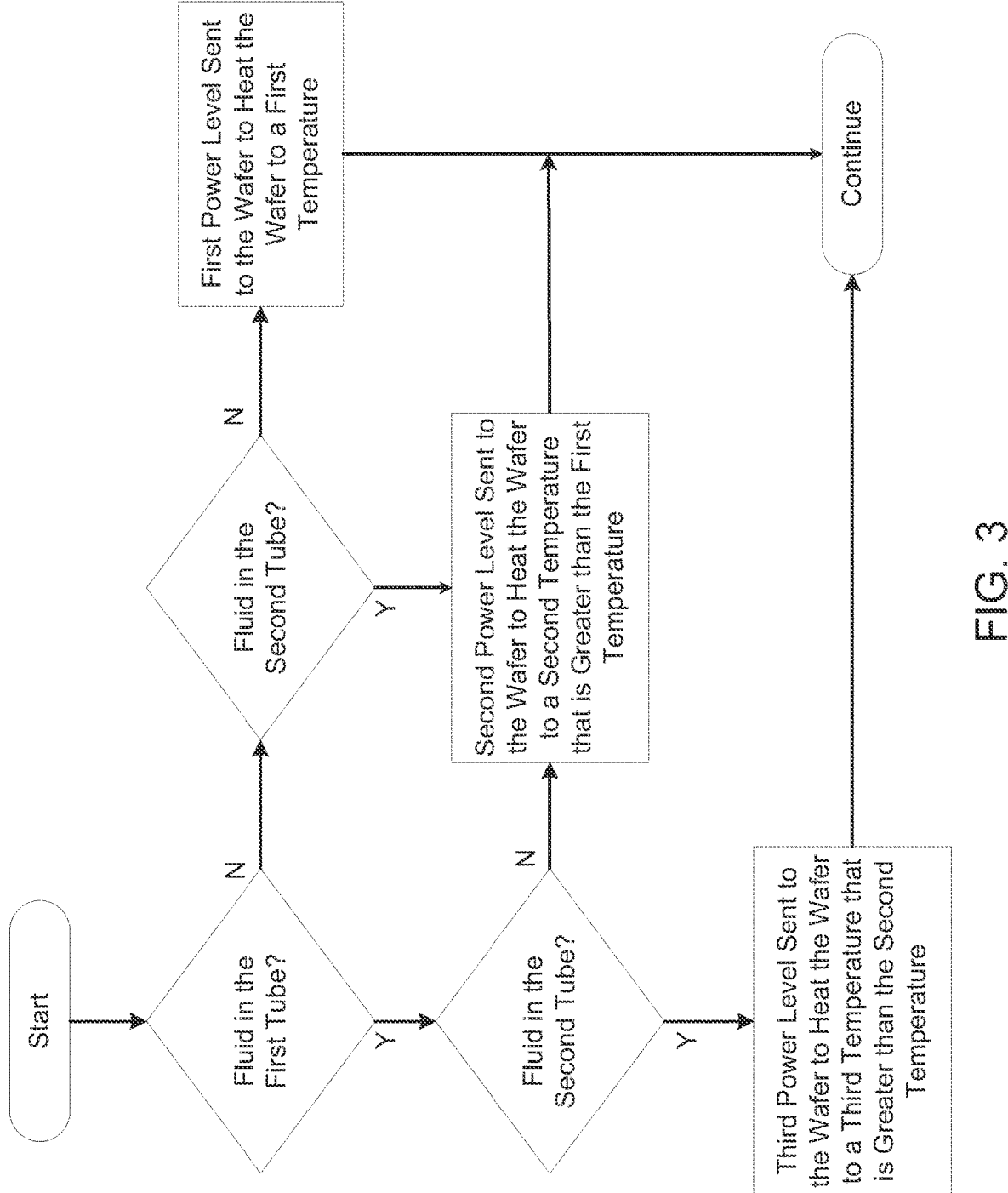

FIG. 2 is a cross-sectional view of a jointed tube, for example, as formed using a tube welding machine, like the example tube welding machine illustrated in FIGS. 1A-1E, in accordance with at least one example embodiment of the present disclosure; and FIG. 3 illustrates a generalize sequence of steps for selecting a tube-joining temperature for use in a tube welding device, like the tube welding device illustrated in FIGS. 1A-1E, in accordance with at least one example embodiment of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In at least one example embodiment, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having" are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers, and/or sections, these elements, components, regions, layers, and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP:

Hypertext Preprocessor), Scala, Eiffel, Smalltalk, Erlang, Ruby, Flash®, Visual Basic®, Lua, MATLAB, SIMULINK, and Python®.

Example embodiments will now be described more fully with reference to the accompanying drawings.

An example tube welding device (also referred to as a tube-joining machine) 100 is illustrated in FIGS. 1A-1E. The tube welding device 100 includes a tube clamp arrangement 102 that is configured to receive at least a portion of a first tube 120 and at least a portion of a second tube 122. The first and second tubes 120, 122 may be connected to bags or similar containers carrying, for example, blood or blood components. In at least one example embodiment, the tube clamp arrangement 102 includes a first tube-holding assembly (which may also be referred to as a first tube-receiving assembly) 110 adjacent to a second tube-holding assembly (also may also be referred to as a second tube-receiving assembly) 112. In at least one example embodiment, the first tube-holding assembly 110 is a first tube-holding clamp, and the second tube-holding assembly 112 is a second tube-holding clamp.

In at least one example embodiment, the first tube-holding assembly 110 may include a first or bottom clamp portion (which may also be referred to as a bottom portion) 130 and a second or top clamp portion (which may also be referred to as a top portion) 140. The bottom clamp portion 130 of the first tube-holding assembly 110 may be movably coupled to the top clamp portion 140 of the first tube-holding assembly 110, such that the first tube-holding assembly 110 may move between a closed position to an open position via the coupling. For example, the bottom clamp portion 130 of the first tube-holding assembly 110 may be fixedly secured to a major plane 104 of the tube welding device 100 and a top clamp portion 140 may be moveable between a first (or closed) clamp state as illustrated, for example, in FIG. 1A and a second (or open) clamp state as illustrated, for example, in FIG. 1B. In at least one example embodiment, a hinge may couple the bottom clamp portion 130 of the first tube-holding assembly 110 and the top clamp portion 140 of the first tube-holding assembly 110.

Similarly, in at least one example embodiment, the second tube-holding assembly 112 may include a first or bottom clamp portion (which may also be referred to as a bottom portion) 132 and a second or top clamp portion (which may also be referred to as a top portion) 142. The bottom clamp portion 132 of the second tube-holding assembly 112 may be movably coupled to the top clamp portion 142 of the second tube-holding assembly 112, such that the second tube-holding assembly 112 may move between a closed position to an open position via the coupling. For example, the bottom clamp portion 132 of the second tube-holding assembly 112 may be fixedly secured to a major surface 104 of the tube welding device 100 and a top clamp portion 142 may be moveable between a first (or closed) clamp state as illustrated in FIG. 1A and a second (or open) clamp state as illustrated in FIG. 1B. In at least one example embodiment, a hinge may couple the bottom clamp portion 132 of the second tube-holding assembly 112 and the top clamp portion 142.

The first and second tube-holding assemblies 110, 112 are each configured to receive at least a portion of first tube 120 and at least a portion of a second tube 122. In at least one example embodiment, for example as illustrated in FIGS. 1B and 1C, the bottom clamp portion 130 of the first tube-holding assembly 110 may include a first tube-receiving crevice or recess or surface 134 configured to receive or engage a first portion of the first tube 120 and a second tube-receiving crevice or recess or surface 136 configured to receive or engage a first portion of the second tube 122. Similarly, the top clamp portion 140 of the first tube-holding assembly 110 may include a first tube-receiving crevice or recess or surface 144 also configured to receive or engage the first portion of the first tube 120 and a second tube-receiving crevice or recess or surface 146 also configured to receive or engage the first portion of the second tube 122. For example, the first tube-receiving crevice 134 of the bottom clamp portion 130 of the first tube-holding assembly 110 may align with the first tube-receiving crevice 144 of the top clamp portion 140 of the first tube-holding assembly 110 to form a first tube-receiving cavity 155 (when the first tube-holding assembly 110 is in a closed state, as illustrated, for example, in FIG. 1A). Likewise, the second tube-receiving crevice 136 of the bottom clamp portion 130 of the first tube-holding assembly 110 may align with the second tube-receiving crevice 146 of the bottom clamp portion 130 of the first tube-holding assembly 110 to form a second tube-receiving cavity 156 (when the first tube-holding assembly 110 is in a closed state, as illustrated, for example, in FIG. 1A).

Like the bottom clamp portion 130 of the first tube-holding assembly 110, the bottom clamp portion 132 of the second tube-holding assembly 112 may include a first tube-receiving crevice or recess or surface 135 configured to receive or engage a second portion of the first tube 120 and a second tube-receiving crevice or recess or surface 137 configured to receive or engage a second portion of the second tube 122. The top clamp portion 142 of the second tube-holding assembly 112 may include a first tube-receiving crevice or recess or surface 145 also configured to receive or engage the second portion of the first tube 120 and a second tube-receiving crevice or recess or surface 147 also configured to receive or engage the second portion of the second tube 122. For example, the first tube-receiving crevice 135 of the bottom clamp portion 132 of the second tube-holding assembly 112 may align with the first tube-receiving crevice 145 of the top clamp portion 142 of the second tube-holding assembly 112 to form a third tube-receiving cavity 165 (when the second tube-holding assembly 112 is in a closed state, as illustrated, for example, in FIG. 1A). Likewise, the second tube-receiving crevice 137 of the bottom clamp portion 132 of the second tube-holding assembly 112 may align with the second tube-receiving crevice 147 of the top clamp portion 142 of the second tube-holding assembly 112 to form a fourth tube-receiving cavity 167 (when the second tube-holding assembly 112 is in a closed state, as illustrated, for example, in FIG. 1A).

The tube welding device 100 may be configured to move one or more portions of the first tube-holding assembly 110 and/or one or more portions of the second tube-holding assembly 112. In at least one example embodiment, the tube welding device 100 may include one or more motorized mechanisms for moving the one or more portions of the first tube-holding assembly 110 and/or one or more portions of the second tube-holding assembly 112. For example, as detailed in the U.S. App. No. 63/455,873, the entire contents of which are herein incorporated by reference.

In at least one example embodiment, the one or more portions of the first tube-holding assembly 110 and/or the one or more portions of the second tube-holding assembly 112 may be movable in a first direction along a major axis of the tube welding machine 100 and/or a second direction along a minor axis of the tube welding machine 100. In at least one example embodiment, for example as illustrated FIG. 1D, the one or more portions of the first tube-holding assembly 110 and one or more portions of the second tube-holding assembly 112 may both be in a first or initial position 150 such that the first tube-receiving cavity 155 of the first tube-holding assembly 110 is aligned with the third tube-receiving cavity 165 of the second tube-holding assembly 112 and the second tube-receiving cavity 156 of the first tube-holding assembly 110 is aligned with the fourth tube-receiving cavity 167 of the second tube-holding assembly 112.

In the initial position 150, the first tube-receiving cavity 155 of the first tube-holding assembly 110 and the third tube-receiving cavity 165 of the second tube-holding assembly 112 aligned therewith may receive adjoining portions of the first tube 120, and the second tube-receiving cavity 156 of the first tube-holding assembly 110 and the fourth tube-receiving cavity 167 of the second tube-holding assembly 112 aligned therewith may receive adjoining portions of the second tube 122, as illustrated for example, in FIGS. 1C and 1D. In at least one example embodiment, the one or more portions of the first tube-holding assembly 110 may be movable relative to the one or more portions of the second tube-holding assembly 112 and/or the one or more portions of the second tube-holding assembly 112 may be movable relative to the one or more portions of the first tube-holding assembly 114, such that, as illustrated in FIG. 1D, a second position 152 is defined, where the first tube-receiving cavity 155 of the first tube-holding assembly 110 is aligned with the third tube-receiving cavity 165 of the second tube-holding assembly 112.

In at least one example embodiment, the tube welding device 100 is configured to receive a wafer 170 within a gap or space between the first tube-holding assembly 110 and the second tube-holding assembly 112. In at least one example embodiment, for example, as illustrated best in FIG. 1D, when the first tube-holding assembly 110 and the second tube-holding assembly 112 are aligned in the initial position 150, the tube welding device 100 may be configured to send energy to the wafer 170 to heat the wafer to a desired temperature (i.e., a tube-joining temperature) and to move the heated wafer 170 from a first non-contact position 172 to a second contact position 174 where the wafer 170 contacts the first and second tubes 120, 122 to temporarily seal together opposing surface of the respective tubes 120, 122 while splitting the tubes into first and second halves 120A, 120B, 122A, 122B and creating molten tube ends (including, for example, first and second molten tube ends 180, 182 for the first tube 120 and first and second molten tube ends 181, 183 for the second tube 122). For example, the heated wafer 170 may cause the portions of the tubes 120, 122 contacted to melt.

In at least one example embodiment, the wafer 170 may be heated using a radiant or conductive heat source the is configured to heat the wafer 170 based on instructions received from a controller. Alternatively, or additionally, the wafer 170 may include an embedded resistive heating element (not shown) and the tube-joining device 100 may be configured to supply an electric current to the embedded resistive heating element based on an instruction received from the controller. In at least one example embodiment, the wafer 170 includes a conductive material, like copper. In at least one example embodiment, the wafer 170 may be a replaceable wafer. For example, the wafer 170 may be removed and replaced after selected use.

In at least one example embodiment, the first and second tubes 120, 122 may be flexible polymer tubes including, for example, thermoplastic materials. The tube-joining temperature may be equal to or greater than the melting point of the material of the first and second tubes 120, 122. That is, the tube-joining temperature should be a temperature that is sufficient to melt an amount of the material of the first and second tubes 120, 122 to create the molten tube ends 180, 181, 182, 183. Tubing that includes fluid, often requires higher tube-joining temperatures. It would be desirable to determine the presence or absence of fluid within the first and second tubes 120, 122 in situ and selecting a best suited tube-joining temperature. For example, when fluid is absent from the first and second tubes 120, 122, the tube welding device 100 may be configured to heat the wafer 170 to a first or lower tube-joining temperature, while when fluid is present in one or both of the first and second tubes 120, 122, the tube welding device 100 may be configured to heat the wafer 170 to a tube-joining temperature that is greater than the first tube-joining temperature. More specifically, when fluid is present in one of the first and second tubes 120, 122 and not the other of the first and second tubes 120, 122, the tube welding device 100 may be configured to heat the wafer 170 to a second tube-joining temperature that is greater than the first tube-joining temperature, and when fluid is present in both of the first and second tubes 120, 122, the tube welding device 100 may be configured to heat the wafer 170 to a third tube-joining temperature that is greater than the second tube-joining temperature. The particular first, second, and third tube-joining temperatures may be predefined and dependent on the particular material selected for the first and second tubes 120, 122.

In at least one example embodiment, one of the first tube-receiving cavity 155 of the first tube-holding assembly 110 and the third tube-receiving cavity 165 of the second tube-holding assembly 112 may include a first fluid detector 190 configured to detect fluid in tube (e.g., tube 120) received by the adjacent first tube-receiving cavity 155 of the first tube-holding assembly 110 and the third tube-receiving cavity 165 of the second tube-holding assembly 112 (for example, as illustrated in FIG. 1C). Similarly, one of the second tube-receiving cavity 156 of the first tube-holding assembly 110 and the fourth tube-receiving cavity 167 may include a second fluid detector 192 configured to detect fluid in tube (e.g., tube 122) received by the adjacent second tube-receiving cavity 156 of the first tube-holding assembly 110 and the fourth tube-receiving cavity 167. For example, as illustrated in FIG. 1E, in at least one example embodiment, the first fluid detector 190 may be disposed within or forming a surface portion of the first tube-receiving crevice 134 of the bottom clamp portion 130 of the first tube-holding assembly 110, and the second fluid detector 192 may be disposed within or forming a surface portion of the second tube-receiving crevice 137 of the bottom clamp portion 132 of the second tube-holding assembly 112.

Although not illustrated, it should be recognized that in other embodiments the first fluid detector 190 (or a portion thereof) may be disposed within or forming a surface portion of the first tube-receiving crevice 144 of the top clamp portion 140 of the first tube-holding assembly 110, the first tube-receiving crevice 135 of the bottom clamp portion 132 of the second tube-holding assembly 112, and/or the first tube-receiving crevice 145 of the top clamp portion 142 of the second tube-holding assembly 112. Although not illustrated, it should be recognized that in other embodiments the second fluid detector 192 (or a portion thereof) may be disposed within or forming a surface portion of the second tube-receiving crevice 147 of the top clamp portion 142 of the second tube-holding assembly 112, the second tube-receiving crevice 136 of the bottom clamp portion 130 of the first tube-holding assembly 110, and/or the second tube-receiving crevice 146 of the bottom clamp portion 130 of the first tube-holding assembly 110.

In at least one example embodiment, the first fluid detector 190 may include any suitable sensor. For example, the sensor of the first fluid detector 190 may include a push switch, a Hall-effect sensor, an optical switch, a magnetic switch, an inductive sensor, a capacitive sensor, an ultrasonic sensor, or any combination thereof. The second fluid detector 192 may similarly include any suitable sensor. For example, the sensor of the second fluid detector 192 may include a push switch, a Hall-effect sensor, an optical switch, a magnetic switch, an inductive sensor, a capacitive sensor, an ultrasonic sensor, or any combination thereof. The first and second fluid detectors 190, 192 may be the same or different.

In at least one example embodiment, the first and second fluid detectors 190, 192 are each configured to provide information regarding the fluid-state of the first and second tubes 120, 122, respectively, to the controller. For example, the first and second fluid detectors 190, 192 may be in electrical communication with the controller. In response, the controller may be configured to select the appropriate temperature—i.e., the first temperature, the second temperature, or the third temperature. In at least one example embodiment, the tube welding device 100 may include a heat source that is in communication with and configured to heat the wafer 170 and the controller may be configured instruct the heat source to supply heat to the wafer 170 to cause the wafer 170 to be heated the selected temperature. In at least one example embodiment, to ensure strong welds, the wafer 170 should be heated while in the first non-contact position 172 and before moving to the second contact position 174.

In at least one example embodiment, the controller may be configured to cause a certain power to be provided to the heat source and/or the wafer 170. For example, as simply illustrated in FIG. 3, when the controller receives information from both the first and second fluid detectors 190, 192 indicating that no fluid is detected, the controller may determine that the first tube-joining temperature is appropriate and cause a first power level to be provided to the heat source and/or the wafer 170; when the controller receives information form one of the first fluid detector 190 and the second fluid detector 192 that fluid is present in one of the first and second tubes 120, 122 and information from the other of the first fluid detector 190 and the second fluid detector 192 that no fluid is present in the other of the first and second tubes 120, 122, the controller may determine that the second tube-joining temperature is appropriate and cause a second power level to be provided to the heat source and/or the wafer 170; and when the controller receives information from both the first and second fluid detectors 190, 192 indicating that both the first and second fluid detectors 190, 192 indicating that third tube-joining temperature is appreciated and cause a third power level to be provided to the heat source and/or the wafer 170. Although not specifically detailed or discussed, it should be appreciated that the generalized processed illustrated in FIG. 3 may include various other steps, including inputs from other detectors assigned U.S. App. No. 63/455,873, the entire contents of which are herein incorporated by reference).

In at least one example embodiment, the tube welding device 100 may include an actuator that is in communication with the controller and that is configured to move the wafer 170 between the first non-contact position 172 and the second contact position 174. After the heated wafer 170 is contacted to the first tube 120 and/or the second tube 122

(i.e., after the welding event and formation of the molten tube ends 180, 181, 182, 183), the wafer 170 may be displaced—for example, returned to its first non-contact position 172 (i.e., retracted)—and the tube welding device 100, as discussed above, may be configured to move the one or more portions of the first tube-holding assembly 110 and/or the one or more portions of the second tube-holding assembly 112 to the second position 152 such that the first molten tube end 180 of the first tube 120 is brought into contact with the second molten tube end 183 of the second tube 122 (and/or the second molten tube end 183 of the second tube 122 is brought into contact with the first molten 180 of the first tube 120) to form a jointed tube 200, as illustrated, for example, in FIG. 2. In at least one example embodiment, the jointed tube 200 may be cooled (for example, passively to room temperature, which is often between about 20° C. and about 22° C.) and subjected to a stress that breaks the temporary seals of the molten tube ends 180, 183 opening the lumen 210 providing fluid communication between the as-joined first and second tubes 120. 122. Methods for applying the stress are illustrated, for example, in U.S. App. No. 63/455,840, the entire contents of which are herein incorporated by reference.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tube welding device for joining two tubes, the tube welding device comprising:

a first tube-holding assembly configured to receive a first portion of a first tube and a first portion of a second tube and including a first detector, the first detector configured to a detect the presence or absence of fluid in the first tube and to generate a first signal indicative of the same;

a second tube-holding assembly configured to receive a second portion of the first tube and a second portion of the second tube and including a second detector, the second detector configured to detect the presence or absence of fluid in the second tube and to generate a second signal indicative of the same;

a wafer disposed between at least a portion the first tube-holding assembly and at least a portion of the second tube-holding assembly, the tube welding device configured to heat the wafer to a tube-joining temperature and to bring the wafer heated to the tube-joining temperature into contact with the first and second tubes; and a controller configured to receive the first and second signals, to select the tube-joining temperature in response to the presence or absence of fluid in the first and second tubes, and to cause an appropriate power level to be sent to the wafer to generate the tube-joining temperature.

2. The tube welding machine of claim 1, wherein when fluid is absent from the first and second tubes, the controller is configured to send a first power level to the wafer to generate a first tube-joining temperature.

3. The tube welding machine of claim 2, wherein when fluid is present in one of the first and second tubes and is absent from the other of the first and second tubes, the controller is configured to send a second power level to the wafer to generate a second tube-joining temperature that is greater than the first tube-joining temperature.

4. The tube welding machine of claim 3, wherein when fluid is present in both of the first and second tubes, the controller is configured to send a third power level to the wafer to generate a third tube-joining temperature that is greater than the second tube-joining temperature.

5. The tube welding machine of claim 1, wherein the first tube-holding assembly includes a first cavity for receiving the first portion of the first tube and a second cavity for receiving the first portion of the second tube.

6. The tube welding machine of claim 5, wherein the second tube-holding assembly includes a third cavity for receiving the second portion of the first tube and a fourth cavity for receiving the second portion of the second tube.

7. The tube welding machine of claim 6, wherein in a first position the first tube-holding assembly is aligned with the second tube-holding assembly such that the first cavity of the first tube-holding assembly is in line with the third cavity of the second tube-holding assembly and the second cavity of the first tube-holding assembly is in line with the third cavity of the second tube-holding assembly.

8. The tube welding machine of claim 7, wherein the first detector is disposed within the first cavity of the first tube-holding assembly, and the second detector is disposed within the fourth cavity of the second tube-holding assembly.

9. The tube welding machine of claim 8, wherein the first tube-holding assembly includes a first bottom portion and a first top portion, the first bottom portion including a first crevice and a second crevice, the first top portion including a third crevice and a fourth crevice, the first crevice of the first bottom portion and the third crevice of the first top portion aligning to form the first cavity, and the second crevice of the first bottom portion and the fourth crevice of the first top portion aligning to form the second cavity;

wherein the second tube-holding assembly includes a second bottom portion and a second top portion, the second bottom portion including a first crevice and a second crevice, the second top portion including a third crevice and a fourth crevice, the first crevice of the second bottom portion and the third crevice of the second top portion aligning to form the third cavity, and the second crevice of the second bottom portion and the fourth crevice of the second top portion aligning to form the fourth cavity; and wherein the first detector is disposed within the first crevice of the first bottom portion of the first tube-holding assembly and the second detector is disposed within the second crevice of the second bottom portion of the second tube-holding assembly.

10. The tube welding machine of claim 8, wherein the first tube-holding assembly includes a first bottom portion and a first top portion, the first bottom portion including a first crevice and a second crevice, the first top portion including a third crevice and a fourth crevice, the first crevice of the first bottom portion and the third crevice of the first top portion aligning to form the first cavity, and the second crevice of the first bottom portion and the fourth crevice of the first top portion aligning to form the second cavity;

wherein the second tube-holding assembly includes a second bottom portion and a second top portion, the second bottom portion including a first crevice and a second crevice, the second top portion including a third crevice and a fourth crevice, the first crevice of the second bottom portion and the third crevice of the second top portion aligning to form the third cavity, and the second crevice of the second bottom portion and the fourth crevice of the second top portion aligning to form the fourth cavity; and wherein the first detector is disposed within the third crevice of the first top portion of the first tube-holding assembly and the second detector is disposed within the fourth crevice of the second top portion of the second tube-holding assembly.

11. The tube welding machine of claim 7, wherein the first detector is disposed within the second cavity of the first tube-holding assembly, and the second detector is disposed within the third cavity of the second tube-holding assembly.

12. The tube welding machine of claim 7, wherein the tube welding device is configured to move the at least a portion of at least one of the first tube-holding assembly and the second tube-holding assembly such that the first tube-holding assembly and the second tube-holding assembly are in a second position where the first cavity of the first tube-holding assembly is brought in line with the fourth cavity of the second tube-holding assembly.

13. The tube welding machine of claim 7, wherein the tube welding device is configured to move the at least a portion of at least one of the first tube-holding assembly and the second tube-holding assembly such that the first tube-holding assembly and the second tube-holding assembly are in a second position where the second cavity of the first tube-holding assembly is brought in line with the third cavity of the second tube-holding assembly.

14. The tube welding machine of claim 1, wherein the first and second detectors each include a push switch, a Hall-effect sensor, an optical switch, a magnetic switch, an inductive sensor, a capacitive sensor, an ultrasonic sensor, or any combination thereof.

15. A method for using a tube welding device, the method comprising:

receiving, by a processor, input from a first sensor aligned with a first clamp configured to receive at least a portion of a first tube, the first sensor configured to detect a presence or absence of fluid in the first tube;

receiving, by a processor, input from a second sensor aligned with a second clamp configured to receive at least a portion of a second tube, the second sensor configured to detect a presence or absence of fluid in the second tube; and supplying, by a processor, power to a wafer disposed between the first clamp and the second clamp, an amount of the supplied power being at a first preselected power level when fluid is absent in both the first tube and the second tube, at a second preselected power level greater than the first power level when fluid is present in one of the first tube and the second tube and absent in the other of the first tube and the second tube, and at a third preselected power level greater than the second power level when fluid is present in both the first tube and the second tube.

16. The method of claim 15, wherein the method further comprises:

moving the wafer, as or after the power is applied the wafer, from a first wafer position to a second wafer position to form a first molten tube end in the first tube and a second molten tube end in the second tube.

17. The method of claim 16, wherein the method further comprises:

moving at least a portion of the first clamp or of the second clamp form a first clamp position to a second clamp position to align and join the first molten tube end and the second molten tube end to form a continuous tube.

18. A method for a preparing a continuous tube from a first tube and a second tube, the method comprising:

heating a wafer disposed between a first clamp configured to receive a portion of a first tube and including a first sensor and a second clamp configured to receive a portion of a second tube and including a second sensor, the first sensor configured to detect a presence or absence of fluid in the first tube, the second sensor configured to detect a present or absence of fluid in the second tube, the wafer heated to a first preselected temperature when fluid is absent in both the first tube and the second tube, a second preselected temperature when fluid is present in one of the first tube and the second tube and absent in the other of the first tube and the second tube, and a third preselected temperature when fluid is present in both of the first tube and the second tube;

as or after the wafer is heated, moving the wafer from a first wafer position to a second wafer position to form a first molten tube end and a second molten tube end; and moving at least a portion of the first clamp position or of the second clamp position from a first clamp position to a second clamp position to align and join the first molten tube end and the second molten tube end to form the continuous tube.

* * * * *